United States Patent [19]

Trenner

[11] Patent Number: 4,781,684

[45] Date of Patent: Nov. 1, 1988

[54] SINGLE USE DISPOSABLE HYPODERMIC SYRINGE

[76] Inventor: Lewis E. Trenner, 3046 S. Gaylord St., Denver, Colo. 80210

[21] Appl. No.: 182,235

[22] Filed: Apr. 15, 1988

Related U.S. Application Data

[63] Continuation-in-part of Ser. No. 92,652, Sep. 3, 1987.

[51] Int. Cl.⁴ .............................................. A61M 5/00
[52] U.S. Cl. ..................................... 604/110; 604/218
[58] Field of Search ............... 604/110, 218, 187, 220, 604/228

[56] References Cited

U.S. PATENT DOCUMENTS

| | | | |
|---|---|---|---|
| 4,233,975 | 11/1980 | Yerman | 604/110 |
| 4,391,272 | 7/1983 | Staempfli | 604/110 |
| 4,493,703 | 1/1985 | Butterfield | 604/110 |
| 4,731,068 | 3/1988 | Hesse | 604/110 |

*Primary Examiner*—John D. Yasko
*Attorney, Agent, or Firm*—Klaas & Law; Joseph J. Kelly

[57] ABSTRACT

A single use disposable hypodermic syringe is provided and comprises a hollow elongated barrel having a generally cylindrical inner surface having a longitudinal axis, an open end and another end having an annular shoulder with a central opening in which a cannula is positioned. A piston and a piston rod are provided and a plug formed from a clear, transparent and resilient but slightly compressible material is releasably secured to the piston and is in sealing relationship with the inner surface of the hollow elongated barrel and, when moved in axial directions functions to aspirate fluid into the hollow elongated barrel or to eject fluid from the hollow elongated barrel. Movement of the plug out of the hollow elongated barrel is prevented by a combination comprising a first portion movable with the plug and a second portion in a fixed position on the inner surface of the hollow elongated barrel and which combination operates only after the plug is in a compressed condition after the fluid has been ejected from the hollow elongated barrel. The first portion can be integral with or separate from the plug and functions in the same manner.

19 Claims, 3 Drawing Sheets

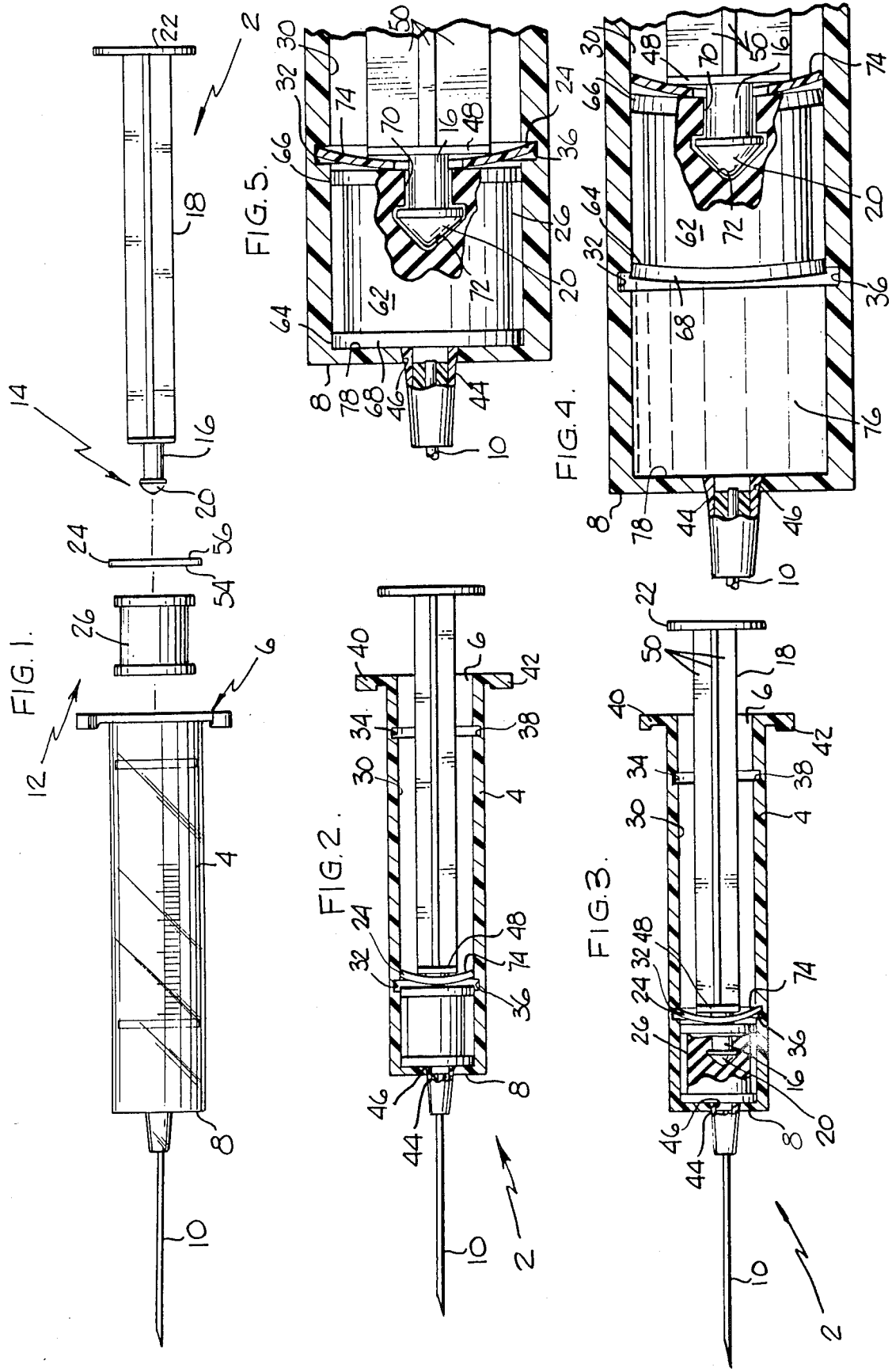

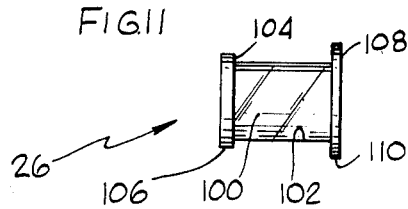
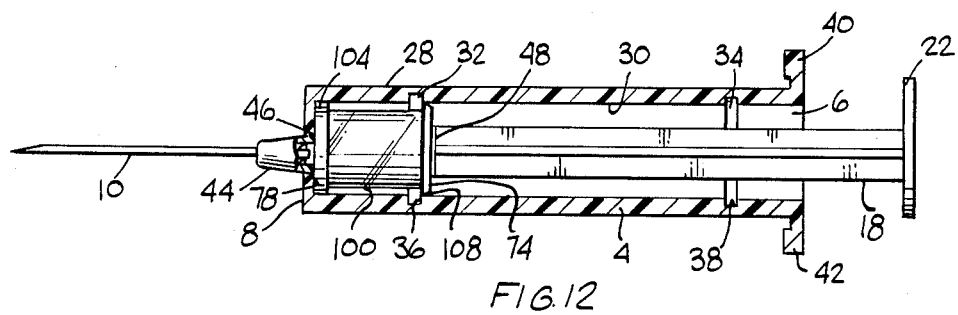
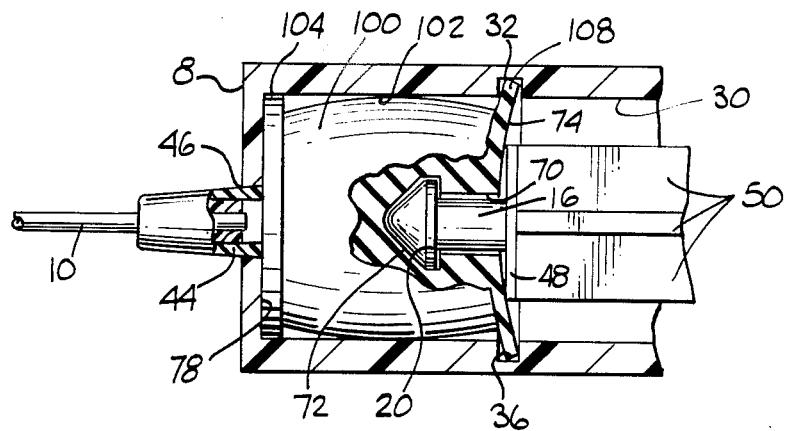
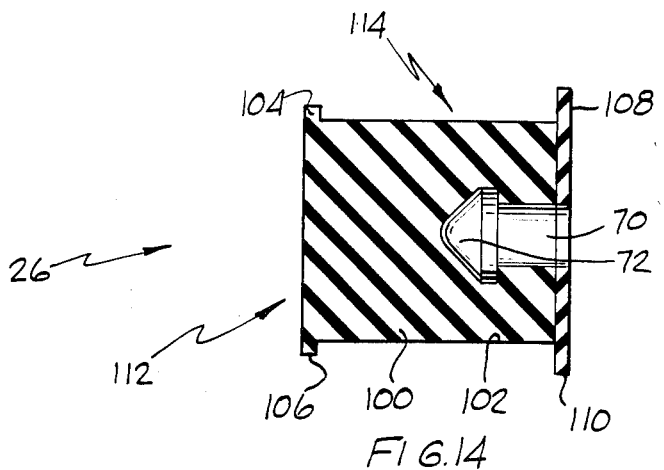

4,781,684

SINGLE USE DISPOSABLE HYPODERMIC SYRINGE

This application is a continuation-in-part of U.S. patent application Ser. No. 092,652 filed Sept. 3, 1987.

FIELD OF THE INVENTION

This invention relates generally to the field of disposable hypodermic syringes which are used to inject a desired fluid into the body for various purposes and more specifically to the field of a single use disposable hypodermic syringe which is particularly suited to prevent the transmission of diseases from one body to another body.

BACKGROUND OF THE INVENTION

There are many instances wherein it is highly desirable that a disposable hypodermic syringe be capable of only a single use. This occurs many times in hospitals or other areas of medical treatment. While great efforts are made to keep disposable hypodermic syringes from being acquired by drug addicts, such efforts are not always successful. Therefore, a single use disposable hypodermic syringe would at least be helpful in preventing the spread of diseases between such drug addicts. The present concern relative to the spread of Acquired Immune Deficiency Syndrome, commonly called AIDS, reaffirms the need for a single use disposable hypodermic syringe. A problem that exists particularly in relation to drug addicts is that the means associated with the disposable hypodermic syringe for permitting only a single use must be of a nature that the function thereof cannot be readily removed by the drug addict. Applicant has provided such a single use disposable hypodermic syringe.

BRIEF DESCRIPTION OF THE INVENTION

This invention provides a single use disposable hypodermic syringe having a conventional barrel means and a plug means mounted therein for use in ejecting fluid out of the barrel means through a cannula means secured to the barrel means. The barrel means is provided with first and second movement preventing means which are spaced apart in an axial direction and cooperate with locking means associated with the plug means to permit movement of the plug means therethrough in an axial direction toward the cannula means but prevent movement of the plug means therethrough in an axial direction away from the cannula means. The first movement preventing means are located near the cannula means so that, when the plug means is fully depressed to eject substantially all of the fluid out of the barrel means, the plug means cannot be moved in an axial direction away from the cannula means. The second movement preventing means are located near the open end of the barrel means to prevent movement of the plug means out of the barrel means after being inserted therein prior to being packaged. The second movement preventing means functions to provide tamper proof protection since the plug means cannot be moved out of the barrel means.

A preferred embodiment of the invention is illustrated in the drawings and comprises a hollow elongated barrel means having a generally cylindrical inner surface, an open end and another end having an annular shoulder with a central opening in which a cannula means, such as a disposable hypodermic needle, is secured. Plug means are releasably secured to a piston means which is integral with a piston rod means for use in moving the plug means in reciprocating axial movements in the hollow elongate barrel means. The plug means is formed from a resilient but slightly compressible material and has a continuous surface facing the cannula means and has at least one continuous cylindrical outer surface in sealing engagement with the generally cylindrical inner surface of the hollow elongated barrel means for drawing fluid into the hollow elongated barrel means and ejecting fluid out of the hollow elongated barrel means. The first and second movement preventing means comprise a combination of elements comprising a first portion comprising locking means which are releasably mounted on the piston means and are located between the plug means and the piston rod means and a second portion comprising first and second axially spaced apart annular radially outwardly extending grooves which are formed in the generally cylindrical inner surface of the hollow elongated barrel means. The first annular groove is located near to but spaced from the cannula means and the second annular groove is located near to but spaced from the open end of the hollow elongated barrel means. Each annular groove has a generally cylindrical inner surface having a diameter greater than the diameter of the generally cylindrical inner surface of the hollow elongated barrel means. The locking means, prior to being inserted into the hollow elongated barrel means, has a generally cylindrical outer surface, oppositely facing generally planar surfaces and an axially extending inner opening. The diameter of the generally cylindrical outer surface of the locking means is greater than the diameter of the generally cylindrical inner surface of each annular groove so that the locking means when inserted into the hollow elongated barrel means will move into the shape of a Belleville washer with its concave side facing the open end of the hollow elongated barrel means. The mounting means for positioning the locking means on the piston means is designed to permit axial movement of the piston means therethrough in either direction as described below. The locking means can be separate from or integral with the plug means.

In operation, the locking means and the plug means are assembled onto the piston means and inserted into the hollow elongated barrel means to a location between the first and second annular grooves. The locking means will move into the shape of a Belleville washer having its concave side facing the open end of the hollow elongated barrel means during the insertion thereof and will permit reciprocating axial movement of the plug means between the first and second annular grooves. The plug means and the locking means have an axial extent slightly greater than the axial extent between the first annular groove and the annular shoulder so that the plug means can be initially moved into contact with the annular shoulder and the locking means will not enter into the first annular groove. After the barrel means has been filled with the desired amount of fluid, the cannula means is inserted into the body of the recipient and the piston means, the locking means and the plug means are moved in an axial direction toward the cannula means to eject the fluid out of the hollow elongated barrel means. When substantially all the fluid has been ejected, the plug means will be compressed a sufficient amount so that the locking means will snap into the first annular groove means and will have the shape of a Belleville washer with its concave side facing the open end of the hollow elongated barrel means so as to prevent movement of the locking means and the plug means in an axial direction away from the cannula means. If a sufficiently great axially outwardly directed force is applied to the piston rod, the piston means will move out of the plug means, move through the locking means and move out of the hollow elongated barrel means leaving the locking means seated in the first annular groove and the plug means between the first annular groove and the cannula means. If an attempt is made to remove the plug means out of the hollow elongated barrel means prior to the use thereof, the locking means will snap into the second annular groove and prevent movement of the plug means in an axial direction away from the cannula means in the same manner as described above in relation to the first annular groove. The hollow elongated barrel means, piston means and the piston rod means are preferably formed from a plastic material such as polypropylene and the locking means, when separate from the plug means, is formed from a plastic material such as a mineral filled polycarbonate or other suitable materials. The plug means alone or when integral with the locking means is preferably formed from a resilient but slightly compressible material that is a clear transparent material such as poly Dimethyl Organo Siloxane or other suitable materials.

BRIEF DESCRIPTION OF THE DRAWING

Illustrative embodiments including the presently preferred embodiment of the invention are shown in the accompanying drawings in which:

FIG. 1 is an exploded view of the various components of the invention;

FIG. 2 is a view with parts in section of a single use disposable hypodermic syringe of this invention prior to aspirating fluid into the barrel means;

FIG. 3 is a view with parts in section of the single use disposable hypodermic syringe of FIG. 2 after the fluid has been ejected;

FIG. 4 is an enlarged view of a portion of the invention as fluid is being ejected;

FIG. 5 is an enlarged view of a portion of FIG. 3;

FIG. 11 is a side elevational view of the preferred embodiment of the plug means;

FIG. 12 is a view similar to FIG. 2 but showing the preferred embodiment of the invention;

FIG. 13 is an enlarged view of a portion of FIG. 12 showing the locking means in a movement preventing position; and FIG. 14 is a cross-sectional view of another embodiment of the invention.

DETAILED DESCRIPTION OF THE INVENTION

Figure 6:
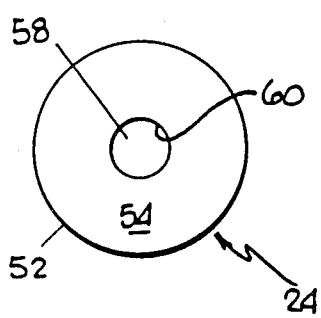
FIG. 6 is a front elevational view of the locking means of FIG. 1.

In FIG. 1, there is illustrated the various components of an embodiment of a single use disposable hypodermic syringe 2 of this invention comprising a hollow elongated barrel means 4 having an open end 6 and another end 8 which is partially closed having a cannula means 10 secured thereto. The plunger means 12 includes a piston means 14 comprising a stem portion 16 having a generally cylindrical outer surface and one end thereof integral with a piston rod means 18 and the other end thereof integral with an enlarged spear head 20 the largest portion thereof having a generally cylindrical outer surface. The piston rod means 18 is provided with an enlarged head portion 22 which is adapted to be grasped by the user. A locking means 24, comprising the first portion of a movement preventing means, has an inner opening, described below, which allows it to be pushed over the enlarged spear head 20 to a location on the stem portion 16. A plug means 26 comprising a resilient but slightly compressible material has a cavity, described below, which is dimensioned to receive the enlarged spear head 20 so that the plug means 26 will move with the piston means 14.

As illustrated in FIGS. 2-5, the hollow elongated barrel means 4 has a generally cylindrical inner surface 30. First 32 and second 34 axially spaced apart annular radially outwardly extending grooves, comprising the second portion of the movement preventing means, are formed in the inner surface 30. The first annular groove 32 has a generally cylindrical inner surface 36 and the second annular groove 34 has a generally cylindrical inner surface 38. The diameter of each generally cylindrical inner surface 36 and 38 is greater than the diameter of the generally cylindrical inner surface 30 of the hollow elongated barrel means 4. A pair of radially outwardly extending flange portions 40 and 42 are integral with the hollow elongated barrel means 4 and are adapted to be contacted by the user when ejecting the fluid from the hollow elongated barrel means 4. The cannula means 10 has an enlarged tapered head portion 44 which is adapted to be press fitted or cemented in a correspondingly tapered opening 46 in the partially closed end 8. Other means may be used for securing the cannula means 10 to the partially closed end 8.

The piston rod means 18 has a generally circular member 48 integral with the one end of the stem portion 16. A plurality of reinforcing fins 50 extend between and are integral with each other and with the generally circular member 48 and the enlarged head portion 22.

The locking means 24 is illustrated in FIGS. 1 and 6 and has a generally cylindrical outer surface 52 and oppositely facing generally planar surfaces 54 and 56. The diameter of the cylindrical outer surface 52 is greater than the diameter of each of the inner surfaces 36 and 38 for a purpose described below. An axially extending inner opening 58 extends through the locking means 24 and has a generally cylindrical inner surface 60. The cross-sectional area of the inner surface 60 is substantially equal to or slightly greater than the largest cross-sectional area of the enlarged spear head 20 so as to permit axial movement of the enlarged spear head 20 therethrough in either direction. As explained below, the locking means 24 may have other initial configurations. The locking means 24 are formed from a material to avoid a permanent set (creep) such as a mineral filled polycarbonate marketed under the trade designation "LEXAN".

The plug means 26 is illustrated particularly in FIGS. 4 and 5 and is formed from a resilient but slightly compressible material and comprises a body portion 62 having a pair 64 and 66 of radially outwardly projecting continuous cylindrical outer surfaces. Each of the outer surfaces 64 and 66 has a diameter slightly greater than the diameter of the generally cylindrical inner surface 30 of the hollow elongated barrel means 4 so as to be in sealing relationship thereto. The end of the body portion 62 facing the cannula means 10 comprises a continuous circular surface 68. As illustrated in FIG. 2, the body portion 62 has an axial extent so that, when the continuous circular surface 68 is in contact with the partially closed end 8 so that there is no dead air space therebetween, the locking means 24 are not in the first annular groove so that the body portion 62 may be moved in an axial direction to aspirate the desired amount of fluid into the hollow elongated barrel means 4. The other end of the body portion 62 has a cylindrical passageway 70 leading to a cavity 72 which is dimensioned similarly to the enlarged spear head 20 so that it may be positioned therein. As illustrated in FIGS. 4 and 5, the enlarged spear head 20 is larger than the passageway 70 so that the plug means 26 will move in either axial direction with the piston means 14. The passageway 70 and the cavity 72 cooperate with the enlarged spear head 20 to releasably secure, as explained below, the plug means 26 to the piston means 14.

The assembled single use disposable hypodermic syringe 2 is illustrated in FIG. 2. At a manufacturing location, the locking means 24 and the plug means 26 are assembled on the piston means 14 to form the plunger means 12 which is then inserted into the hollow elongated barrel means 4. The diameter of the outer surface 52 of the locking mean 24 is greater than the diameter of the generally cylindrical inner surface 30 of the hollow elongated barrel means 4 so that when the plunger means 12 is pushed into the hollow elongated barrel means 4, the locking means 24 is forced into the shape of a Belleville washer with its concave side 74 facing the open end 6 of the hollow elongated barrel means 4. If desired, the locking means 24 could be in the shape of a Belleville washer with its largest diameter being greater than the diameter of each of the generally cylindrical inner surfaces 36 and 38. The plunger means 12 is inserted into the hollow elongated barrel means 4 until the plug means 26 are in contact with the partially closed end 8 and the locking means 24 are spaced slightly from the first annular groove 32. The single use disposable hypodermic syringe is then packaged for marketing.

In use, the single use disposable hypodermic syringe 2 is removed from the package and the cannula means 10 is exposed and inserted into a container having the fluid that is to be inserted into the body. The plunger means 12 are then actuated to fill the hollow elongated barrel means 4 with the desired amount of fluid 76. While the single use disposable hypodermic syringe is designed not to have any entrapped air, it is desirable to remove any possible entrapped air in the conventional manner. The cannula means 10 is then inserted into the body that is to receive the fluid 76. The plunger means 12 are then moved toward the cannula means 10, as illustrated in FIGS. 2 and 4, to eject the fluid 76 through the cannula means 10. During the ejection of the fluid 76 from the hollow elongated barrel means 4, as illustrated in FIGS. 3 and 5, the plug means 26 will move against the annular shoulder 78 of the another end 8 and be compressed, as illustrated in FIGS. 3 and 5 by the bulging body portion 62, a sufficient amount so that the locking means 24 will snap into the first annular groove 32 and move into contact with the generally cylindrical inner surface 36 thereof. The locking means 24 is in a shape of a Belleville washer with its concave side facing the open end 6 of the hollow elongated barrel means 4 so as to provide substantial resistance to movement in an axial direction away from the cannula means 10. Therefore, movement of the plug means 26 in an axial direction away from the cannula means 10 is prevented. The resistance to movement in an axial direction away from the cannula means 10 provided by the locking means 24 in the shape of the Belleville washer seated in the first annular groove 32 is substantially greater than the resistance to axial movement provided by the enlarged spear head 20 in the cavity 72 and the passageway 70 so that, if sufficient force is applied to the piston rod 18 in an axial direction away from the cannula means 10, the enlarged spear head 20 will be pulled out of cavity 72, through the passageway 70 and through the inner opening 58 of the locking means 24 and out of the hollow elongated barrel means 10. The locking means 24 will remain seated in the first annular groove 32, as illustrated in FIG. 5, and the plug means 26 will remain in the position between the locking means 24 and the annular shoulder 78. When the locking means 24 is seated in the annular groove 32, the slightly compressed plug means 26 will exert a force on the locking means 24 to ensure that it is firmly seated in the annular groove 32.

If an attempt is made to move the plunger means 12, in the assembly as illustrated in FIG. 2, in an axial direction away from the cannula means 10, the locking means 24 will snap into the second annular groove 34 and into contact with the generally cylindrical inner surface 38 so as to prevent further axial movement in that direction in the same manner as described above when the locking means 24 snapped into the first annular groove 32 to provide tamper proof protection so that the plug means 26 cannot be removed and deleterious materials inserted into the hollow elongated barrel means. If such movement of the locking means 24 into the second annular groove 34 was accidental, the nature of the locking means 24 in the shape of a Belleville washer will permit movement thereof in an axial direction toward the cannula means 10.

Figure 7:
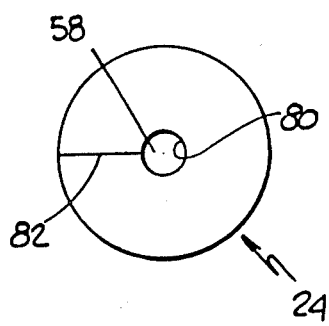
FIG. 7 is a modification of the locking means.

In FIG. 7, there is illustrated a modification of the locking means 24 wherein the inner surface 80 of the inner opening 58 has a diameter substantially equal to the diameter of the cylindrical outer surface of the stem portion 16 so that the longitudinal axes of the stem portion 16 and the locking means 24 coincide. A separation 82 is formed in the locking means 24 to provide for the axial movement of the enlarged spear head 20 therethrough in either axial direction.

Figure 8:
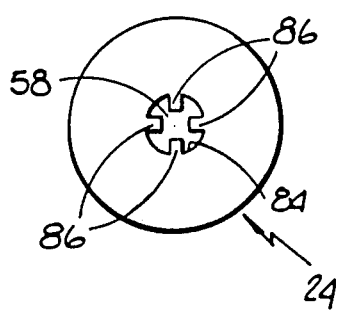
FIG. 8 is another modification of the locking means.

In FIG. 8, there is illustrated another modification of the locking means 24 wherein the inner surface 84 of the inner opening 58 has a plurality of radially inwardly extending fingers 86 having end portions adapted to be tangent to the outer cylindrical surface of the stem portion 16 so that the longitudinal axes of the stem portion 16 and the locking means 24 coincide. The fingers 86 are sufficiently flexible to permit the axial movement of the enlarged spear head 20 therethrough in either axial direction.

Figure 9:
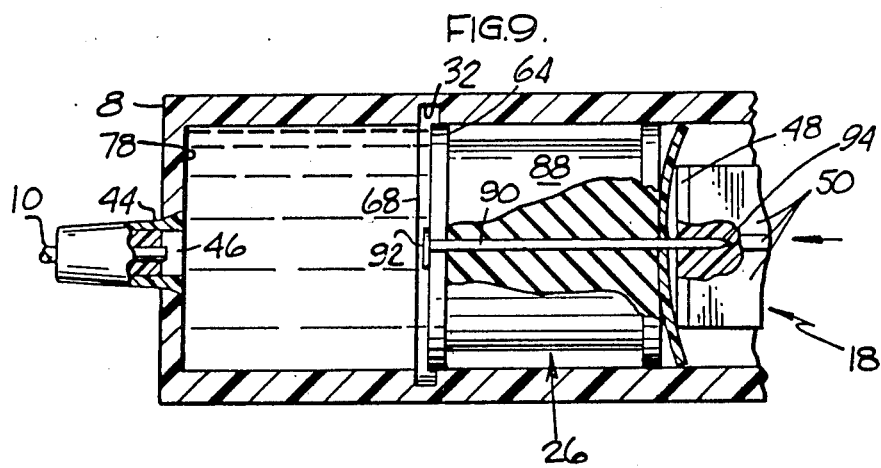
FIG. 9 is a view similar to FIG. 4 but showing another embodiment of the invention.
Figure 10:
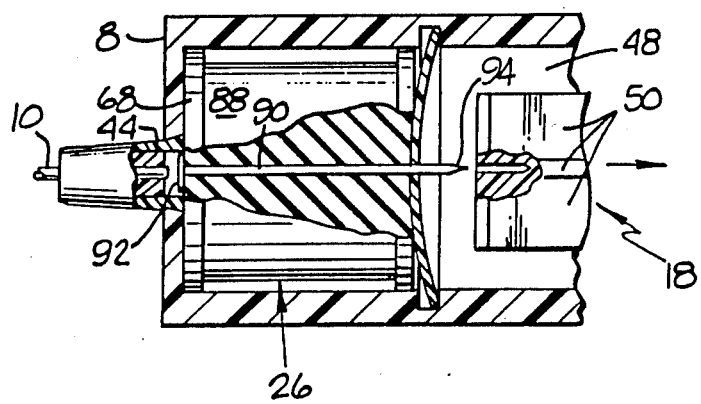
FIG. 10 is a view similar to FIG. 5 but showing the embodiment of FIG. 9 after the fluid has been ejected and with the piston means separated from the piston rod means.

Another embodiment of the invention is illustrated in FIGS. 9 and 10. The body portion 88 of the plug means 26 is formed without the passageway 70 and the cavity 72. Also, the piston means 14 does not have the stem portion 16 and the enlarged spear head 20. The plug means 26 and the locking means 24 are releasably secured to the piston rod means 18 by a pin means 90 having an enlarged head portion 92 and a pointed piercing portion 94. Prior to being inserted into the hollow elongated barrel means 4, the locking means 24 and the plug means 26 are positioned against the circular member 48 and a pin means 90 is pushed through the body portion 88, the locking means 24 and into the piston rod means 18 until the enlarged head 92 contacts the continuous circular surface 68. The resilient but slightly compressible nature of the body portion 88 forms a seal around the pin means 90. A sufficient portion of the pin means 90 next to the pointed piercing portion 94 is frictionally engaged with the surrounding portions of the piston rod means 18 so as to permit the axially reciprocating movement of the plunger means 12 to fill the hollow elongated barrel means 4 with the desired amount of fluid 76. As illustrated in FIG. 10, after the locking means 24 has snapped into the first annular groove 32 and a sufficient amount of radially outwardly directed force is applied to the piston rod means 18, the circular member 48 will be separated from the pin means 90 so that the locking means 24, the plug means 26 and the pin means 90 will remain in the hollow elongated barrel means 4 between the first annular groove 32 and the cannula means 10. The plug means 26 illustrated in FIGS. 9 and 10 is similar in structure and functions as the plug means 26 in FIGS. 2-5 in that in its uncompressed state it will position the locking means 24 slightly from the first annular groove 32 but in its compressed state, as illustrated in FIG. 10 by the bulging body portion 88, will permit the locking means 24 to snap into the first annular groove 32.

In FIGS. 11-13, there is illustrated a preferred embodiment of the invention wherein the plug means 26 comprises a central body portion 100 having a generally cylindrical outer surface 102, an integral radially outwardly projecting portion 104 having a generally cylindrical outer surface 106 and an integral radially outwardly projecting portion 108 having a generally cylindrical outer surface 110. The diameter of the generally cylindrical outer surface 106 is slightly greater than the diameter of the generally cylindrical inner surface 30 of the hollow elongated barrel means 4 so as to be in a sealing relationship therewith. However, the diameter of the generally cylindrical outer surface 106 is not great enough that it would stop movement of the plug means 26 in either directions past the first annular groove 32 or the second annular groove 34. The diameter of the generally cylindrical outer surface 110 is slightly greater than the diameter of the inner surface 36 of the first annular groove 32 and the diameter of the inner surface 38 of the second annular groove 34 so that the radially outwardly projecting portion 108 functions as a locking means in the same manner as the locking means 24. In the preferred embodiment of the invention, the plug means 26 is integrally formed using a resilient but slightly compressible clear transparent material, such as a poly Dimethyl Organo Siloxane, such as that marketed by Dow Corning under the trade designation Sylgard 186, modified by up to ten percent by weight of a silicone oil, such as that marketed by Dow Corning under the trade designation Silicone Oil 100 or other materials having similar characteristics. The plug means 26 has a Shore A durometer of between about 25 and 35.

As illustrated in FIG. 12, the central body portion 100, the portion 104 and the portion 108 have an axial extent which is greater than the axial extent between the annular shoulder 78 and the annular groove 32 so that the portion 104 may be moved into contact with the annular shoulder 78 and provide some resistance to further movement of the plug means 26 so as to properly position the plug means 26 so that the cylindrical outer surface 110 is spaced in an axial direction away from the annular shoulder 78 a slight distance away from the annular groove 32. Also, the portion 104 and the cylindrical outer surface 106 ensure that no dead air space exists between them and the annular shoulder 78. This permits the piston rod means 18 to be able to be moved in an axial direction away from the annular shoulder 78 so that the plug means 26 can aspirate the desired fluid into the hollow elongated barrel means 4. However, when the fluid is ejected, the plug means 26 will be compressed, as illustrated in FIG. 13 by the bulging outer surface 102, so that the cylindrical outer surface 110 will enter into the annular groove 32 to prevent axial movement of the plug means 26 in a direction away from the annular shoulder 78 so that no additional fluid can be aspirated into the hollow elongated barrel means 4. When the radially outwardly projecting portion 108 is seated in the annular groove 32, the slightly compressed plug means 26 will exert a force on the radially outwardly projecting portion 108 to ensure that it is firmly seated in the annular groove 32. As described above, if sufficient forces are applied to the piston rod means 18, the enlarged spear head 20 will be pulled out of the cavity 72 leaving the plug means 26 in the position illustrated in FIG. 13.

If desired, the radially outwardly projecting portion 108 could be a separate member having the same size and shape and performing the same locking functions and secured to the central body portion 100 by suitable means such as by gluing. Another alternative, illustrated in FIG. 14, is to form the plug 26 from a composite material so that the plug 26 has a front portion 112 comprising the radially outwardly projecting portion 104 and the central body portion 100 and a rear portion 114 comprising the radially outwardly projecting portion 108. In this alternative, the central body portion 100 and the radially outwardly projecting portion 104 would be molded first and then the rear portion 114 would be molded thereto. The rear portion 114 would be molded from a clear transparent material to have a Shore A durometer of about 50 and the front portion 112 would be molded from a clear transparent material to have a Shore A durometer of about 35. This relatively soft front portion 112 would permit the hypodermic syringe to be shipped from the manufacturing facility, as described above, but would ensure that the locking means 108 would move past the first annular groove 32 when fluid was being injected into the user.

The modification illustrated in FIGS. 11-13 functions in the same manner as the hypodermic syringe illustrated in FIGS. 1-5. At a manufacturing location, the plug means 26, comprising the central body portion 100 and the radially outwardly projecting portions 104 and 108, the piston means 14, the plunger means 12 are assembled and inserted into the hollow elongated barrel means 4. The diameter of the generally cylindrical outer surface 110 of the locking means comprising the radially outwardly projecting portion 108 is greater than the diameter of the generally cylindrical inner surface 30 of the hollow elongated barrel means 4 so that when the plunger means 12 is pushed into the hollow elongated barrel means 4, the radially outwardly projecting portion 108 is forced into the shape of a Belleville washer with its concave side 74 facing the open end 6 of the hollow elongated barrel means 4 so that the plug 26 can be moved in both directions along the inner cylindrical surface 30 but can move past the first and second annular grooves 32 and 34 only in one direction. The plunger means 12 is inserted into the hollow elongated barrel means 4 until the plug means 26 are in contact with the annular shoulder 78 of the another end 8 and the radially outwardly projecting portion 108 is spaced slightly from the first annular groove 32 in a direction away from the annular shoulder 78. The single use disposable hypodermic syringe, as illustrated in FIG. 12, is then packaged for marketing.

In use, the single use disposable hypodermic syringe 2 is removed from the package and the cannula means 10 is exposed and inserted into a container having the fluid that is to be inserted into the body. The plunger means 12 are then actuated to fill the hollow elongated barrel means 4 with the desired amount of fluid 76. While the single use disposable hypodermic syringe is designed not to have any entrapped air, it is desirable to remove any possible entrapped air in the conventional manner. The cannula means 10 is then inserted into the body that is to receive the fluid 76. The plunger means 12 are then moved toward the cannula means 10, to eject the fluid 76 through the cannula means 10. During the ejection of the fluid 76 from the hollow elongated barrel means 4, the plug means 26 will move against the shoulder 78 and be compressed a sufficient amount so that the radially outwardly projecting portion 108 will snap into the first annular groove 32 and move into contact with the generally cylindrical inner surface 36 thereof. The radially outwardly projecting portion 108 is in a shape of a Belleville washer with its concave side facing the open end 6 of the hollow elongated barrel means 4 so as to provide substantial resistance to movement in an axial direction away from the cannula means 10. Therefore, movement of the plug means 26 in an axial direction away from the cannula means 10 is prevented. The resistance to movement in an axial direction away from the cannula means 10 provided by the radially outwardly projecting portion 108 in the shape of the Belleville washer seated in the first annular groove 32 is substantially greater than the resistance to axial movement provided by the enlarged spear head 20 in the cavity 72 and the passageway 70 so that, if sufficient force is applied to the piston rod 18 in an axial direction away from the cannula means 10, the enlarged spear head 20 will be pulled out of cavity 72, through the passageway 70 and out of the hollow elongated barrel means 10. The radially outwardly projecting portion 108 will remain seated in the first annular groove 32, as illustrated in FIG. 13, and the plug means 26 will remain in the position between the annular groove 32 and the annular shoulder 78.

If an attempt is made to move the plunger means 12, in the assembly as illustrated in FIG. 12, in an axial direction away from the cannula means 10, the radially outwardly projecting portion 108 will snap into the second annular groove 34 and into contact with the generally cylindrical inner surface 38 so as to prevent further axial movement in that direction in the same manner as described above when the radially outwardly projecting portion 108 snapped into the first annular groove 32 to provide tamper proof protection so that the plug means 26 cannot be removed and deleterious materials inserted into the hollow elongated barrel means. If such movement of the radially outwardly projecting portion 108 into the second annular groove 34 was accidental, the nature of the radially outwardly projecting portion 108 in the shape of a Belleville washer will permit movement thereof in an axial direction toward the cannula means 10.

In one embodiment of the invention, illustrated in FIGS. 1-5, the hollow elongated barrel means has an external axial extent of about 2.175 inches, an internal axial extent of about 2.150 inches, an outer diameter of about 0.325 inch, an inner diameter of about 0.245 inch. Each of the inner surfaces 36 and 38 has a diameter of about 0.270 inch and the axial extent of each of the first 32 and second 34 annular grooves is about 0.025 inch. The mid-point of the first annular groove 32 is spaced from the shoulder 78 a distance of about 0.350 inch and the mid-point of the second annular groove 34 is spaced from the open end 6 a distance of about 0.260 inch. The diameter of the outer surface 110 of the portion 108 is about 0.295 inch. It is understood that the foregoing description is of one embodiment only and that the single use disposable hypodermic syringe of this invention can be made in many different sizes and tolerances.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A single use disposable hypodermic syringe comprising:
   a hollow elongated barrel means having an inner surface, at least one open end and another end for use in providing a container for a fluid;
   said hollow elongated barrel means having a longitudinal axis;
   piston means mounted in said hollow elongated barrel means for reciprocation therein along said longitudinal axis;
   plug means on said piston means and in sealing engagement with said inner surface and used to aspirate fluid into said hollow elongated barrel means and to eject said fluid from said hollow elongated barrel means and having at least a portion thereof formed from a resilient but slightly compressible material;
   piston rod means secured to said piston means and projecting outwardly from said hollow elongated barrel means through said at least one open end for use in reciprocating said piston means;
   said another end having a radially inwardly extending wall portion having a central opening, said radially inwardly extending wall portion providing an annular shoulder for providing a stop for said plug means;
   cannula means connected to said central opening;
   movement preventing means comprising a first portion movable with said plug means and a second portion in a fixed position on said inner surface of said hollow elongated barrel means; and
   said plug means and said first portion having a longitudinal extent greater than the longitudinal extent between said annular shoulder and said second portion so that, when said plug means contacts said annular shoulder and is uncompressed, said second portion will be located between said first portion and said annular shoulder to permit movement of said plug means away from and toward said annular shoulder, but, when said plug contacts said annular shoulder and is compressed, said first portion is located between said second portion and said annular shoulder and in contact with said second portion to prevent movement of said plug means in a direction away from said annular shoulder.

2. The invention as in claim 1 wherein:
said first portion is integral with said plug means.

3. The invention as in claim 2 wherein:
said first portion and said plug means are formed from a clear transparent material.

4. The invention as in claim 3 wherein:
said inner surface is cylindrical;
said second portion having a cylindrical inner surface having a diameter greater than the diameter of said inner surface of said hollow elongated barrel means so as to form abutment means therebetween; and
said first portion is cylindrical having a diameter greater than the diameter of said cylindrical inner surface of said second portion prior to being inserted into said hollow elongated barrel means.

5. The invention as in claim 4 wherein:
said second portion comprises an annular groove in said inner surface of said hollow elongated barrel means.

6. The invention as in claim 5 and further comprising:
means located between said second portion and said open end for preventing removal of said plug means from said hollow elongated barrel means.

7. The invention as in claim 6 and further comprising:
securing means for releasably securing said plug means to said piston means so that the axially directed forces required to move said first portion past said second portion toward said open end is greater than the axially directed forces required to separate said piston means from said plug means so that, upon the application of sufficient axially outwardly directed forces on said piston rod means, said piston means will move out of said hollow elongated barrel means leaving behind said plug means including said first portion.

8. The invention as in claim 2 wherein:
said inner surface is cylindrical;
said second portion having a cylindrical inner surface having a diameter greater than the diameter of said inner surface of said hollow elongated barrel means so as to form abutment means therebetween; and
said first portion is cylindrical having a diameter greater than the diameter of said cylindrical inner surface of said second portion prior to being inserted into said hollow elongated barrel means.

9. The invention as in claim 8 wherein:
said second portion comprises an annular groove in said inner surface of said hollow elongated barrel means.

10. The invention as in claim 9 and further comprising:
means located between said second portion and said open end for preventing removal of said plug means from said hollow elongated barrel means.

11. The invention as in claim 10 and further comprising:
securing means for releasably securing said plug means to said piston means so that the axially directed forces required to move said first portion past said second portion toward said open end is greater than the axially directed forces required to separate said piston means from said plug means so that, upon the application of sufficient axially outwardly directed forces on said piston rod means, said piston means will move out of said hollow elongated barrel means leaving behind said plug means.

12. The invention as in claim 11 wherein:
said plug means and said first portion comprising a composite elastomeric material with said first portion having a durometer greater than the durometer of said plug means.

13. The invention as in claim 12 wherein:
said plug means is slightly compressible.

14. The invention as in claim 1 wherein:
said first portion is separate from said plug means; and
said first portion has the shape of a Belleville washer having its concave side facing said open end of said hollow elongated barrel means.

15. The invention as in claim 14 wherein:
said inner surface is cylindrical;
said second portion having a cylindrical inner surface having a diameter greater than the diameter of said inner surface of said hollow elongated barrel means so as to form abutment means therebetween; and
said first portion is cylindrical having a diameter greater than the diameter of said cylindrical inner surface of said second portion prior to being inserted into said hollow elongated barrel means.

16. The invention as in claim 15 wherein:
said second portion comprises an annular groove in said inner surface of said hollow elongated barrel means.

17. The invention as in claim 16 and further comprising:
means located between said second portion and said open end for preventing removal of said plug means from said hollow elongated barrel means.

18. The invention as in claim 17 and further comprising:
securing means for releasably securing said plug means and said first portion to said piston means so that the axially directed forces required to move said first portion past said second portion toward said open end is greater than the axially directed forces required to separate said piston means from said plug means and said first portion so that, upon the application of sufficient axially outwardly directed forces on said piston rod means, said piston means will move out of said hollow elongated barrel means leaving behind said plug means and said first portion.

19. The invention as in claim 18 wherein:
said plug means, when in said compressed condition, exerts a force urging said first portion against said second portion.

* * * * *